US008396545B2

(12) United States Patent
Berridge et al.

(10) Patent No.: US 8,396,545 B2
(45) Date of Patent: Mar. 12, 2013

(54) ELECTROPHYSIOLOGICAL SCREENS FOR COGNITIVE MODULATORS

(75) Inventors: Craig W. Berridge, Madison, WI (US); David M. Devilbiss, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 808 days.

(21) Appl. No.: 12/391,406

(22) Filed: Feb. 24, 2009

(65) Prior Publication Data

US 2009/0312624 A1    Dec. 17, 2009

Related U.S. Application Data

(60) Provisional application No. 61/031,094, filed on Feb. 25, 2008.

(51) Int. Cl.
*A61B 5/05* (2006.01)
*A61B 5/484* (2006.01)

(52) U.S. Cl. ..................... 600/544; 600/554
(58) Field of Classification Search ............... None
See application file for complete search history.

(56) References Cited

PUBLICATIONS

Drouin et al (J Neurophysiol, 2006, 96:622-632, IDS).*
Berridge et al (Biol Psychiatry, 2006, 60:11110112, IDS).*
Devilbiss and Berridge (The J of Pharmacology, 2006, 319:1327-1335).*
Korostenskaja et al (Psychopharmacology 2008, 197:475-486, published online Feb. 9, 2008).*
Kahkonen et al (Neuropsychopharmacology, 2001, 25:499-504).*
Arnsten and Li, "Neurobiology of Executive Functions: Catecholamine Influences on Prefrontal Cortical Functions," *Biol. Psychiatry*, 57:1377-1384 (2005).
Berridge et al., "Methylphenidate Preferentially Increases Catecholamine Neurotransmission within the Prefrontal Cortex at Low Doses that Enhance Cognitive Function," *Biol. Psychiatry*, 60:1111-1120 (2006).
Buzsaki, "Rhythms of the Brain," Oxford University Press, USA (2006).
Cohen and Cuffin, "Demonstration of Useful Differences Between Magnetoencephalogram and Electroencephalogram," *Electroencephalogr. Clin. Neurophysiol.*, 56:38-51 (1983).
Drouin et al., "Methylphenidate Enhances Noradrenergic Transmission and Suppresses Mid- and Long-Latency Sensory Responses in the Primary Somatosensory Cortex of Awake Rats," *J. Neurophysiol.*, 96:622-632 (2006).
Fuster, "The Prefrontal Cortex: Anatomy, Physiology, and Neuropsychology of the Frontal Lobe," 3$^{rd}$ ed., Lippincott, Williams & Wilkins (1997).
Klausberger et al., "Brain-State- and Cell-Type-Specific Firing of Hippocampal Interneurons in vivo," *Nature*, 421:844-848 (2003).
Greenhill, "Clinical Effects of Stimulant Medication in ADHD," *Stimulant Drugs and ADHD: Basic and Clinical Neuroscience*, Oxford University Press, New York (2001).
Miller and Cohen, "An Integrative Theory of Prefrontal Cortex Function," *Annu. Rev. Neurosci.*, 24:167-202 (2001).

* cited by examiner

*Primary Examiner* — Laura B Goddard
(74) *Attorney, Agent, or Firm* — Foley & Lardner LLP

(57) ABSTRACT

Methods, apparatuses, and systems for analysis of electromagnetic activity of prefrontal cortex neurons in subjects are provided. The methods, apparatuses, and systems of the present invention can be used as a means to screen for cognitive modulators. They can be used to predict the effects of compounds such as psychostimulants and other drugs on prefrontal cortex-dependent cognition.

19 Claims, 5 Drawing Sheets

ELECTROPHYSIOLOGICAL SCREENS FOR COGNITIVE MODULATORS

CROSS-REFERENCE TO RELATED APPLICATIONS

This invention claims priority to U.S. Provisional Patent Application Ser. No. 61/031,094, filed Feb. 25, 2008, which is herein incorporated by reference.

GOVERNMENT INTERESTS

This invention was made with United States government support awarded by the National Institutes of Health (NIH), grants No. DA000389 and MH014602. The United States government has certain rights in this invention.

FIELD OF THE INVENTION

This invention relates to electrophysiology, and more particularly to novel electrophysiological screens for cognitive modulators.

BACKGROUND

The prefrontal cortex (PFC) is the anterior part of the frontal lobes of the brain, lying in front of the motor and premotor areas. The prefrontal cortex plays a critical role in higher cognitive function. Dysregulation of prefrontal cortex-dependent cognition is associated with a variety of disorders and conditions, including Attention Deficit/Hyperactivity Disorder (ADHD) and normal aging.

There are limited pharmacological treatments available that improve prefrontal cortex-dependent cognition. Psychostimulants, such as methylphenidate (MPH; Ritalin®) and amphetamine, are the most effective and widely used class of drugs for the treatment of ADHD. The therapeutic effects of these drugs are strongly linked to their ability to improve cognitive processes dependent on the prefrontal cortex (Greenhill, 2001, *Stimulant Drugs and ADHD: Basic and Clinical Neuroscience*, Oxford University Press, New York).

The ability of MPH and other psychostimulants to enhance PFC-dependent cognition is observed in both normal and ADHD-affected individuals. However, despite their effectiveness in treating ADHD, there are a number of potential serious risks and potential adverse actions associated with the use of stimulants, including abuse. Given these risks, there is tremendous interest in developing non-psychostimulant drugs for use in the treatment of ADHD and other disorders or conditions associated with impairment in PFC-dependent cognition. In particular, there is a need for non-stimulant drugs that improve PFC-dependent cognition.

Currently, the degree to which a chemical compound improves prefrontal cortex-dependent cognition is assessed by administering the compound to animal or human test subjects and measuring performance in standard behavioral tests of PFC-dependent cognition, such as working memory (Arnsten and Li, 2005, *Biol. Psychiatry* 57: 1377-1384). This is a labor-intensive procedure that requires extensive training and expertise. It would be advantageous to provide faster methods of assessing the potential facilitatory actions of a compound on PFC-dependent cognition. The present invention provides this and related needs.

BRIEF SUMMARY

Provided are methods of testing subjects to predict effects of administered compounds on the subjects' prefrontal cortex-dependent cognition. The methods include: administering a compound; subsequently administering a stimulus that evokes an electromagnetic response in the subject's prefrontal cortex (such as evoking an electrical and/or magnetic response in the subject's prefrontal cortex); sensing at least one component of the electromagnetic response in the subject's prefrontal cortex (such as sensing one or both of an electrical or a magnetic response) in response to the administered stimulus, both in the presence and in the absence of the compound; comparing at least one component of the electromagnetic response evoked by the stimulus in the absence of the administered compound with at least one component of the electromagnetic response evoked by the stimulus in the presence of the administered compound; and determining the effect of the administered compound based on the comparison. The method may include determining the effect by correlating the at least one component of the electromagnetic response evoked by the stimulus with the effect of the administered compound on the subjects' prefrontal cortex-dependent cognition. The methods may be practiced where the at least one component of the electromagnetic response is an electrical component.

The methods may be practiced where the stimulus is selected from the group consisting of electrical, magnetic, photic, auditory, or mechanical stimulation of the subjects' nervous systems. The methods may be practiced where the sensing of at least one component of the electromagnetic response includes attaching at least one recording electrode to or above the subject's prefrontal cortex. The methods may be practiced where the sensing of at least one component of the electromagnetic response includes measuring field potentials of the prefrontal cortex using magnetoencephalographic recording or electroencephalographic recording. The methods may be practiced where the administration of a stimulus includes electrical stimulation of the subject's hippocampus. The electrical stimulation may be with a current in the range of between about 0.01 mA (milliAmpere) to about 10.0 mA, with duration of between about 0.01 ms (milliseconds) and about 10.0 ms, and with a frequency of between about 0.1 Hz (Hertz) and about 10.0 Hz. The administered compound may enhance PFC-dependent cognition. Alternatively, the administered compound may impair PFC-dependent cognition. In the practice of the methods, sensing at least one component of the electromagnetic response in the subject's prefrontal cortex in response to the administered stimulus in the absence of the compound may include administering the stimulus; and sensing at least one component of the electromagnetic response, the sensing being performed prior to administering the compound. Administering the stimulus may be performed during sensing at least one component of the electromagnetic response in order to obtain at least one component of the electromagnetic response prior to, during, and after administering the stimulus.

Provided are methods of testing a subject to predict the effects of administered compounds on the subject's prefrontal cortex-dependent cognition, where the methods include: administering a compound; subsequently administering a stimulus that evokes an electromagnetic response in the subject's prefrontal cortex; sensing of at least one component of the electromagnetic response in the subject's prefrontal cortex both in the absence and in the presence of the compound; comparing at least one component of the electromagnetic response evoked by the stimulus in the presence of the administered compound to the electromagnetic response evoked by the electrical when a known cognition modulator is administered to the subject; and predicting the effect of the administered compound on the subject's prefrontal cortex-dependent cognition based on the at least one component of the electromagnetic response. In the practice of the methods, the known cognition modulator may be methylphenidate. The methods may be practiced where the stimulus is selected from the group consisting of electrical, magnetic, photic, auditory, or mechanical stimulation of the subject's nervous system. The methods may be practiced where the sensing of the electromagnetic response includes attaching at least one recording electrode to or above the subject's prefrontal cortex. The methods may be practiced where the sensing of at least one component of the electromagnetic response includes measuring field potentials of the prefrontal cortex using electroencephalography recording. The methods may be practiced where the administration of a stimulus includes electrical stimulation of the subject's hippocampus. The electrical stimulation may be with a current in the range of between about 0.01 mA (milliAmpere) to about 10.0 mA, with duration of between about 0.01 ms (milliseconds) and about 10.0 ms, and with a frequency of between about 0.1 Hz (Hertz) and about 10.0 Hz.

Provided are systems for determining an effect of a compound that modulates prefrontal cortex-dependent cognition. The systems include: a recording electrode for detecting at least one component of an electromagnetic response in the prefrontal cortex of a subject; a stimulation electrode for evoking the at least one component of the electromagnetic response in the subject's prefrontal cortex; a recording module for receiving and recording the at least one component of the electromagnetic response from the recording electrode in the subject's prefrontal cortex in response to an administered stimulus from the stimulation electrode both in the presence and in the absence of the compound; and an analytical module for analyzing the recorded component of the electromagnetic response in the subject's prefrontal cortex in response to the administered stimulus both in the presence and in the absence of the compound in order to determine an effect of the administered compound. The systems may include detection of at least one component of the electromagnetic response by measuring field potentials of the prefrontal cortex. The systems may include detection of at least one component of the electromagnetic response includes using magnetoencephalographic recording or electroencephalographic recording. The systems may include means for evoking the electromagnetic response that include electrical stimulation of the subject's hippocampus. In the systems, electrical stimulation may be with a current in the range of between about 0.01 mA (milliAmpere) to about 10.0 mA, with duration of between about 0.01 ms (milliseconds) and about 10.0 ms, and with a frequency of between about 0.1 Hz (Hertz) and about 10.0 Hz. The systems may detect compounds that enhance PFC-dependent cognition. Alternatively, the systems may detect compounds that impair PFC-dependent cognition.

DETAILED DESCRIPTION OF THE PRESENTLY PREFERRED EMBODIMENTS

Figure 1:
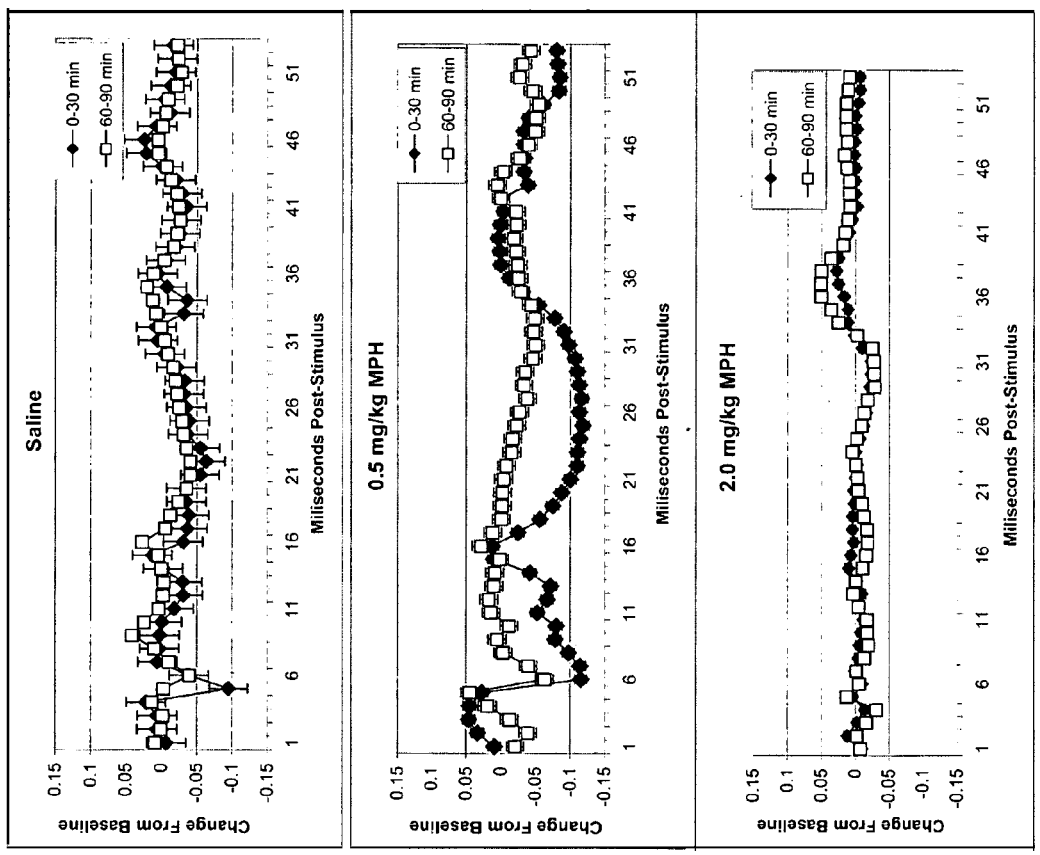
FIG. 1 depicts graphs showing the effects of 0.5 mg/kg methylphenidate (MPH), 2.0 mg/kg MPH, and saline (control injection) on the evoked response-potential recorded in the ipsilateral hemisphere of the prefrontal cortex following electrical stimulation of the ventral subiculum of the hippocampus in a rat.

Provided are methods for analysis of electrical activity of PFC neurons in subjects. The methods can be used to predict the effect of drugs, such as psychostimulants, on PFC-dependent cognition. For example, the present invention could be used to assay the degree to which candidate drug compounds will modulate, e.g. enhance or impair PFC-dependent cognition.

"Prefrontal cortex (PFC)" refers to the anterior part of the frontal lobes of the brain, lying in front of the motor and premotor areas.

"Cognitive modulator", as used in this application, is a compound that can modulate the cognitive ability of a subject. "Cognitive ability" is an ability of a subject that relates to the process of acquiring knowledge by using reasoning, intuition, or perception. Cognitive modulators include compounds that can act as cognitive enhancers, i.e. they can enhance, or improve, the cognitive ability of a subject (such as methylphenidate and amphetamine); and compounds that can impair cognition (such as scopolamine).

"Enhancing" or "improving" the cognitive ability of a subject means improving performance in standard tests of higher cognitive function including memory, cognitive flexibility sustained attention, and planning, to a similar or greater degree than that observed with drugs approved for the treatment of ADHD. "Impairing" the cognitive ability of a subject means reducing performance in standard tests of higher cognitive function including, long-term memory, cognitive flexibility sustained attention, and planning below levels of normal populations. "Enhancement" of prefrontal cortex-dependent cognition refers to improvement in performance on tests typically used to assess prefrontal-dependent cognitive function, including tests of working memory, response inhibition, cognitive flexibility, etc. "Impairment" of prefrontal cortex-dependent cognition refers to reducing performance in standard tests of higher cognitive function including, including tests of working memory, response inhibition, cognitive flexibility, etc.

"Psychostimulant", as used in this application, is a compound such as a drug having arousal-increasing, locomotor-activating, stereotypy and reinforcing/euphoria-inducing actions when administered at sufficiently high doses. A psychostimulant may act to block the reuptake of monoamines to varying degree e.g. methylphenidate (MPH) or amphetamine.

The electrical activity generated by cells in the brain can be monitored by directly recording the electrical activity produced by many cells within the brain. This electrophysiological signal is related to the sum of all dendritic synaptic activity within a cerebral location. Monitoring this electrophysiological signal from electrodes placed on the scalp refers to an electroencephalogram (EEG). Monitoring this electrophysiological signal from electrodes placed directly on the brain surface refers to an electrocorticogram (ECoG). Monitoring this electrophysiological signal from electrodes placed directly within a brain region such as the PFC refers to a "field potential" recording. The EEG/ECoG/field potential is comprised of a mixture of frequencies of oscillations ranging from approximately 0.01-200 Hz (Buzsaki, 2006 *Rhythms of* the Brain, Oxford University Press, USA). This maximal voltage of this signal that can be recorded from the scalp (EEG) is approximately 200 µV (microvolt), which is dependent on the frequencies present. This signal can increase approximately 3 orders of magnitude when electrodes are placed directly on the brain surface (ECoG). The difference between single-neuron electrophysiological measurements and field potential measurements is described below.

The electrical activity generated by cells in the brain can be monitored by indirectly recording the magnetic fields produced by the electrical activity of many cells within the brain. Monitoring this magnetophysiological signal from electrodes placed on the scalp refers to a magnetoencephalogram (MEG). The MEG signal is approximately 1000 fT (femtotesla) when measured from the scalp. The relationship between MEG and EEG, as well as distinctions between these electro-magnetic-physiological signals are well described (Cohen and Cuffin, 1983, *Electroencephalogr. Clin. Neurophysiol.* 56:38-51).

"Evoked-response potential" (ERP) or "evoked potential", as used in this application, is an electrical response monitored in the form of a change in electrical potential or magnetic field. The ERP refers to the electrical or magnetic signal recorded from a tested subject, such as a human or animal, that is a summation or average of this signal across repeated presentation of a stimulus. The ERP is distinct from spontaneous potentials such as electroencephalograms, magnetoencephalogram, or electromyograms. Averaged evoked potential amplitudes are similar in magnitude to EEG/ECoG field potential recordings range from less than a microvolt to several microvolts). In the practice of the preferred embodiment of the present invention, in response to electrical stimulation (range 50-5000 µA) of the hippocampus, evoked-response potentials can be measured in the PFC.

"Electromagnetic response" refers to a response that relates to, and/or is produced by electromagnetism. Electromagnetic response can be produced through neuronal activity, which is an electrical current that produces a magnetic field. The electromagnetic response may include electrical and magnetic components.

"Electroencephalography" (EEG) refers to the measurement of the electrical activity produced by the brain. In particular, EEG refers to the recording of the brain's rhythmic electrical activity as recorded from pairs of electrodes placed on the scalp. "Magnetoencephalography" is similar to an electroencephalography but records oscillations in magnetic fields produced by the brain.

The term "stimulus", as used in this application, refers to an external event or change in the environment that generates a response. In a preferred example of the present invention, the stimulus can be an electrical current pulse delivered to the hippocampus that generates a response that is measured in the subject's PFC. In some embodiments, the stimulus can be an electrical or magnetic pulse of a region of the subject's nervous system that elicits a response in the subject's prefrontal cortex. In some embodiments, the stimulus may include, but is not limited to, the administration of electrical, magnetic, photic, auditory, or mechanical stimulation of the subject's nervous system; the administration of the stimulus (or stimuli) elicits a response in the subject's prefrontal cortex. Various combinations of two or more of the above stimuli may also be used for stimulation of the subject's central and/or peripheral nervous system in order to elicit a response in the subject's prefrontal cortex.

The term "nervous system" is meant to include both the peripheral nervous system and the central nervous system. In some preferred embodiments, stimulus (or stimuli) may be applied to only one type of nervous system, e.g. only to the peripheral nervous system.

Clinically-relevant doses of MPH may increase catecholamine (norepinephrine and dopamine) neurotransmission selectively within the prefrontal cortex (Berridge et al., 2006, *Biol. Psychiatry* 60: 1111-1120). This suggests an important role of the prefrontal cortex in the therapeutic actions of low-dose psychostimulants. Importantly, this effect is not observed within the somatosensory cortex, the non-PFC region of the cortex (see also Drouin et al., 2006, *J. Neurophysiol.* 96: 622-632). Selective targeting of prefrontal cortical catecholamines is not observed with moderately higher doses of MPH that do not improve PFC-dependent cognition.

In the practice of the present invention, detection of the electrical response (i.e., measurement of evoked-response potentials) can be performed in a variety of ways, including but not limited to, attaching at least one electrode to the subject's prefrontal cortex, attaching at least one electrode within the subject's prefrontal cortex, attaching at least one electrode on the surface of the subject's prefrontal cortex, attaching at least one electrode above the subject's prefrontal cortex, or using various combinations thereof, so long as the measured electrical response is the evoked-response potential in the prefrontal cortex, which is evoked in response to electrical stimulation as described herein. As used herein, reference to "attaching an electrode to the PFC" specifically includes all of the above ways of attachments of electrodes to the subjects. The present invention can additionally be practiced but not limited to using other detectors, such as magnetometers, to measure the evoked response of magnetic fields.

The "prefrontal cortex" is a brain region that includes the anterior part of the frontal lobes of the brain, lying in front of the motor and premotor areas. In humans this region is similar in function to the PFC in non-human primates and the frontal cortex in rodents. The term "prefrontal cortex" (PFC) as used in this application includes this functionally similar brain region regardless of species.

The "hippocampus" is a brain region that provides substantial input into the PFC. As well, "hippocampus", as used in this application, includes the cells of the hippocampus and the connections from the subject's hippocampus to the subject's PFC, as they provide an excitatory input from the hippocampus to the PFC. This definition of the hippocampus includes, but is not limited to, the subdivisions and extensions of the hippocampus such as those commonly known as the dentate gyrus, CA1, CA2, CA3, ventral and dorsal subiculum.

The term "subject", as used in this application, refers to mammals, and especially to humans and nonhuman animals, domesticated animals, laboratory animals, and the like. The methods of the present invention can be used with any of these subjects.

The term "conduit", as used in this application, refers to a means of conveying something from one location to another. A conduit allows for data transmission, which can be accomplished in a variety of ways (electrical, telemetry, optical tether, etc.). For example, an electrical conduit is an electrical data transmission system used for providing transfer of electrophysiological signals between a recording electrode (or electrodes) and a control module. Electrical conduit may be made of a variety of materials, e.g. metal, plastic, fiber, or fired clay.

In one aspect, the present invention provides an easy-to-implement electrophysiological screen for detection of drug/compound dependent changes (both improvement and impairment) in PFC-dependent cognition by examining drug-induced changes in the components of the evoked response-potential recorded in the PFC in subjects in response to electrical stimulation of the hippocampus. In one preferred example, this assay records electrical field potentials within the prefrontal cortex of unanesthetized subjects in response to electrical stimulation of the ventral subiculum of the hippocampus. These field potentials, monitored as evoked-response potentials (ERPs), are an easily obtained electrical signal the acquisition of which does not require extensive training or expensive equipment.

In another aspect, the present invention provides an easy-to-implement screen for detection of drug/compound dependent changes (both improvement and impairment) in PFC-dependent cognition by examining drug-induced changes in the components of the electrical or magnetic evoked response recorded in the PFC in subjects in response to activation of this region by means of electrical, magnetic, photic, acoustic, or mechanical stimulation of the central and/or peripheral nervous system.

It has been discovered that cognition-modulating doses of compounds such as psychostimulants alter the magnitude of specific components of this evoked-response potential. Thus, a variety of compounds can be electrophysiologically tested for their capacity to influence (enhance or impair) PFC-dependent cognition.

In one preferred example, the subject tested can be a laboratory animal, e.g. a rodent such as a male Sprague-Dawley rat, with a mass of about 150-500 g. However, this screen for cognitive modulators, by extension, is not solely limited to use in laboratory animals such as rats, but may also include mice, canines, non-human primates, and humans. For humans, the assays can be performed by eliciting an ERP within the PFC using noninvasive means, e.g. human cognitive testing (Wisconsin Card Sorting, Stroop, Sustained Attention; etc.), transcranial magnetic stimulation, etc.

Generally, dosages and routes of administration of the compounds that are tested as candidate cognitive modulators will be determined according to the size and condition of the subject, and in accordance with standard pharmaceutical practices. Dose levels employed can vary widely, and can readily be determined by those of skill in the art. Typically, amounts in the milligram up to gram quantities are employed. The compounds that are tested for cognitive modulation may be administered to a subject by various routes, e.g. orally, transdermally, perineurally, or parenterally, that is, by intravenous, subcutaneous, intraperitoneal, or intramuscular injection.

Provided are methods, apparatuses, and systems that can be used as drug discovery tools, to identify compounds that have an effect on PFC-dependent cognition. Generally, candidate compounds are administered to a subject, a suitable stimulus (e.g. electrical stimulus) is administered, and electrical brain activity is monitored in the PFC. The stimulus may be repeatedly administered. In one preferred example, a suitable stimulus is an electrical current pulse that can be generated in a variety of ways using standard readily available current sources typically used in electrophysiological neuroscience research, e.g. by electrically stimulating the hippocampus, a brain region that provides substantial input into the PFC. In this preferred example, the electrical stimulus can be a bi-polar square wave approximately 0.01-10 mA as measured at peak current, of 0.01-10 ms duration, at 0.1-10.0 Hz. Such an electrical stimulus in the hippocampus should generate an evoked potential that is measured in the subject's PFC. In some embodiments, it may be possible to measure the evoked potential above the subject's PFC, using recording electrodes placed on the brain surface, skull or scalp. In some embodiments, it may be possible to measure the evoked magnetic field above the subject's PFC, using magnetometers placed on or near the brain surface, skull or scalp. The intensity, duration, and frequency of electrical stimulation applied to the hippocampus can be adjusted to a level that is optimal for measurements of the evoked potentials according to the present invention. In some embodiments, adjustment of these parameters may result in levels of evoked potentials where the monitored parameters can readily be compared between treatments.

Not wanting to be bound by the following explanation, the electrical potential changes of the present invention are likely related to the actions of one or more neurotransmitters via binding at their receptors. Thus, the methods of the present invention can be used to assay for a variety of neurotransmitters and their receptors, e.g. catecholamines and/or gamma-aminobutyric acid (GABA), in both normal and artificially-generated (e.g., transgenic animals) subjects. Additionally, these methods may be useful for assessing the potential cognitive actions of other physical or biochemical entities that influence neuron function (e.g. proteins, glial cells, RNA).

In the practice of the present invention, instead of single-unit (i.e., single-neuron) recordings, it is preferred to record evoked-response potentials (ERPs) in the form of a field potential, an EEG-like signal generated from large populations of neurons, within the PFC. This field potential is an easily obtained signal that does not require extensive training or expensive equipment. Thus, standard EEG recording equipment can be used for these recordings in the PFC. Electrodes for monitoring such PFC electrical activity can be placed either directly into the PFC (animal subjects) or above the PFC.

In the practice of the present invention, instead of single-unit (i.e., single-neuron) recordings, it can be preferred to record evoked-response potentials in the form of a magnetic field potential, a MEG-like signal generated from the cumulative magnetic field of a large population of neurons, within the PFC. This magnetic field potential has distinct properties to EEG and is a non-invasive technique. Standard MEG recording equipment can be used for these recordings in the PFC. Devices for monitoring such PFC magnetic activity can be placed directly above the PFC.

Provided are methods that can be used to predict and/or detect the actions of cognition-modulating compounds in experimental subjects, without the need for behavioral testing. In some preferred embodiments, acquiring ERP recordings from test subjects according to the present invention is well-suited for drug discovery programs. Specifically, one or more of the following indicators (markers) can be used to predict the degree to which an administered compound will influence PFC-dependent cognition in a subject: 1) in one example, statistically-significant changes in the magnitude of the first two components of the evoked response potential (initial biphasic function of this potential) predict the cognitive actions of the administered compound; 2) in another example, statistically-significant changes in a third component of the evoked potential (magnitude of the function between the third and fourth zero crossing of the function) predict the cognitive actions of the administered compound.

"Statistically significant change" refers to the statistical comparison of ERP recordings with and without drug where the test can reject the null hypothesis that the two conditions are the same. Any one of these indicators, or a combination of two or more of these indicators, can be used to compare the electrical response evoked by the electrical stimulus in the absence of the administered compound with an electrical response evoked in the presence of the administered compound.

In an example of the methods of the present invention, the electromagnetic response was characterized as a decrease of approximately 0.1 mV in the early components (5-50 msec) of the evoked response recorded from unanesthetized rats in which field potential recording electrodes (50 μm diameter, ~50,000 Ohm-5,000,000 Ohm were implanted directly into the prefrontal cortex; FIG. 1).

The apparatuses and systems for practicing the present invention can be automated, e.g., using a computer, and appropriate software can be developed for monitoring and analyzing the output from the recording electrode (or electrodes). Such software can perform multiple functions related to analyzing the sensed, or recorded, electrical and/or magnetic responses. "Analyzing" the electromagnetic responses using software refers to one or more of recording, storing, displaying, quantifying, filtering, retrieving, and comparing one or more of the evoked electrical responses. For example, the software may be used for recording and storing the electromagnetic responses evoked by the stimulus for comparison between administered compounds. The software may also be used for cataloging the electromagnetic responses evoked by the stimulus.

The computer may comprise one or more computer systems, with each computer system comprising a processor and a memory that can communicate via a bus. The memory may include volatile and/or non-volatile memory, and may include one or more programs, including the software discussed above. The memory may be a main memory, a static memory, or a dynamic memory. The memory may include, but may not be limited to, computer-readable storage media such as various types of volatile and non-volatile storage media including, but not limited to, random access memory, read-only memory, programmable read-only memory, electrically programmable read-only memory, electrically erasable read-only memory, flash memory, magnetic tape or disk, optical media and the like. In one case, the memory may include a cache or random access memory for the processor. Alternatively or in addition, the memory may be separate from the processor, such as a cache memory of a processor, the system memory, or other memory. The memory may be an external storage device or database for storing data. Examples may include, but are not limited to, a hard drive, compact disc ("CD"), digital video disc ("DVD"), memory card, memory stick, floppy disc, universal serial bus ("USB") memory device, or any other device operative to store data. The memory may be operable to store instructions executable by the processor. The functions, acts or tasks illustrated in the figures (such as FIGS. 2-5) or described herein may be performed by the programmed processor executing the instructions stored in the memory. The functions, acts or tasks may be independent of the particular type of instruction set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

The computer system may further include a display, such as a liquid crystal display (LCD), an organic light emitting diode (OLED), a flat panel display, a solid state display, a cathode ray tube (CRT), a projector, a printer or other now known or later-developed display device for outputting determined information. The display may act as an interface for the user to see the functioning of the processor, or specifically as an interface with the software stored in the memory or in the drive unit.

Additionally, the computer system may include an input device configured to allow a user to interact with any of the components of system. The input device may be a number pad, a keyboard, or a cursor control device, such as a mouse, or a joystick, touch screen display, remote control or any other device operative to interact with the system.

The computer system may also include a disk or optical drive unit. The disk drive unit may include a computer-readable medium in which one or more sets of instructions, e.g. software, can be embedded. Further, the instructions may perform one or more of the methods or logic as described herein. The instructions may reside completely, or at least partially, within the memory and/or within the processor during execution by the computer system. The memory and the processor also may include computer-readable media as discussed above. For example, the instructions to perform the actions illustrated in FIGS. 2-5 (described below) may be included in the memory.

The present disclosure contemplates a computer-readable medium that includes instructions or receives and executes instructions responsive to a propagated signal. The instructions may be implemented with hardware, software and/or firmware, or any combination thereof. Further, the instructions may be transmitted or received over the network via a communication interface. The communication interface may be a part of the processor or may be a separate component. The communication interface may be created in software or may be a physical connection in hardware. The communication interface may be configured to connect with a network, external media, the display, or any other components in system, or combinations thereof. The connection with the network may be a physical connection, such as a wired Ethernet connection or may be established wirelessly as discussed below. Likewise, the additional connections with other components of the system may be physical connections or may be established wirelessly.

When testing candidate compounds, comparisons can be made with evoked potentials recorded upon administration to the subject of compounds already in use for the treatment of ADHD (e.g., Ritalin®, Adderall®, and Straterra®) and other disorders or conditions associated with impairment in PFC-dependent cognition.

In particular, it is contemplated that the methods of the present invention can find use in a variety of applications, including: 1) development of new and less risky drugs for the treatment of ADHD and other conditions/disorders associated with PFC dysfunction (for example, sleep deprivation, a condition common to military, medical and other professions); and 2) use in drug discovery programs to screen for drugs that might impair PFC-dependent cognition.

In one aspect, the present invention provides for monitoring field potential recordings (i.e., field potentials). "Field potential recordings" are EEG-like evoked-response potential (ERP) from the PFC recording electrodes. These field potentials are as easy to obtain and analyze as regular EEG signals.

Doses of MPH that improve PFC-dependent working memory significantly alter early components of the ERP recorded in the PFC in the range of about 1 ms to about 500 ms post-stimulus. In the example shown in FIG. 1, significant effects of methylphenidate are observed in the range of 1 ms to 40 ms post-stimulus. The significant effects of methylphenidate on the ERP are only observed at doses (e.g. 0.5 mg/kg) and times (0-30 min after compound administration) that elicit improvements in PFC-dependent working memory. Higher doses that do not improve PFC-dependent cognition do not significantly affect this ERP. Thus, this assay predicts the cognition-enhancing effects of MPH.

ADHD is treated by other compounds (some psychostimulants like methylphenidate and some not psychostimulants, such as tricyclic antidepressants and atomoxetine). In some aspects of the invention, the methods described herein should be effective for detecting drugs of varying categories that will have the same cognition-enhancing actions.

"Stimulation electrode" refers to an electrode that current is passed through to elicit an activation of cells within the vicinity of the electrode.

"Recording electrode" refers to an electrode that measures the difference in electrical potential between the electrode and a reference or ground point.

In one example of the present invention, one or more recording electrodes are used to monitor the electrical activity of the prefrontal cortex. For example, one or more recording electrodes are inserted into the prefrontal cortex. In one preferred example, these recording electrodes can be inserted into the prelimbic region of the PFC of a male Sprague-Dawley rat, with a mass of about 150-500 g. Examples of useful PFC coordinates for insertion of recording electrodes are (but are not limited to): A +3.0±1.0 mm; L 0.8±0.3 mm; V −3.0. For these coordinates, A refers to the anterior dimension relative to the fiduciary of Bregma, L refers to the lateral dimension relative to the midline skull landmark and V refers to the ventral direction as measured from the surface of the brain. Alternatively, one or more recording electrodes can be inserted into other subregions of the PFC. When more than one electrode is used for recording, the electrodes may be inserted into different subregions of the PFC. For example, one recording electrode may be inserted in a prelimbic region, whereas another electrode may be inserted into infralimbic or orbitofrontal regions, etc. One or more stimulation electrodes are inserted into the subiculum/CA1 region of the hippocampus (for example into coordinates corresponding to A −6.7±0.3; L 5.5±0.3; V −6.5±0.3). The stimulation electrode or electrodes may be inserted into any other location along this afferent pathway. Generally, what is important is that the applied stimulus evokes a measurable electrical response in the subject's prefrontal cortex. For more information on the anatomy and the function of the prefrontal cortex, see, e.g. Fuster, 1997, *The Prefrontal Cortex Anatomy, Physiology, and Neuropsychology of the Frontal Lobe*, 3$^{rd}$ ed., Lippincott, Williams & Wilkins; Miller and Cohen, 2001, *Annu. Rev. Neurosci.* 24: 167-202.

Figure 2:
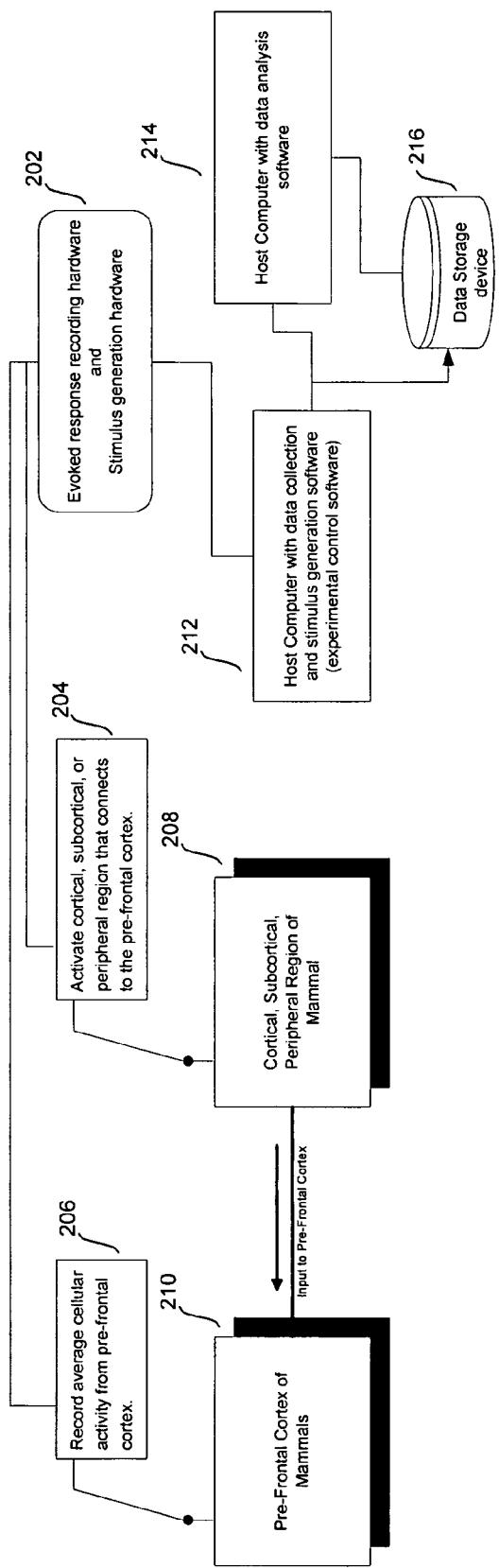
FIG. 2 is a block diagram of the general model and the hardware of the system utilized in connection with the methods of the present invention.
Figure 3:
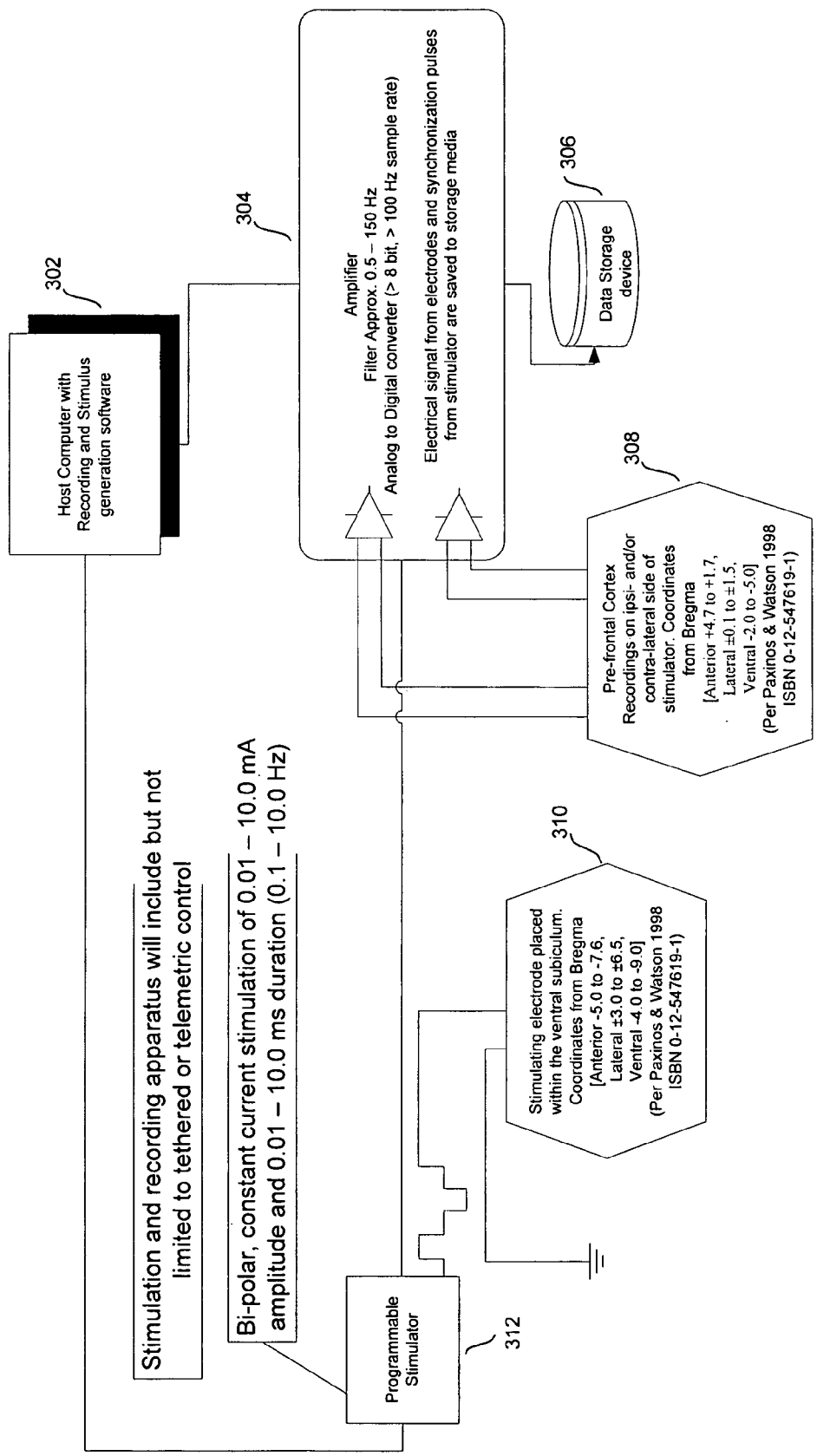
FIG. 3 is a block diagram of the surgical model and the hardware of the system utilized in connection with the methods of the present invention.

FIGS. 2 and 3 are exemplary block diagrams of the general model and the hardware of the system utilized in connection with the methods of the present invention. Responses of the pre-frontal cortex to input from cortical, subcortical, or peripheral regions that are connected to the prefrontal cortex may be recorded, stored and analyzed using a computer-based system.

FIG. 2 is a block diagram of the general model and the hardware of the system utilized in connection with the methods of the present invention. The embodiment in FIG. 2 shows schematically the evoked stimulus recording hardware and the stimulus generation hardware 202. The hardware 202 is used to activate the cortical, subcortical, and/or peripheral region that connects to the prefrontal cortex 204. At least a part of the cellular activity from the prefrontal cortex may be recorded, e.g. the average cellular activity from the prefrontal cortex is recorded 206. The cortical, subcortical, or peripheral region of mammals 208 provides input to the prefrontal cortex of mammals 210. In this preferred embodiment, a host computer with data collection and stimulus generation software (experimental control software) 212 may be connected to a host computer with data analysis software 214 and with a data storage device 216.

Hippocampal stimulation elicits ERPs in both hemispheres of the PFC (ipsilateral and contralateral, relative to the hippocampal stimulation electrode), thus providing flexibility in positioning of the measuring electrode (or electrodes). The evoked electrical potentials are referenced to a ground electrode. When used in experimental animals (e.g. rats) and one or more electrodes are inserted into the PFC, the electrodes are held in place with acrylic cement and the subjects are typically allowed to recover for 5-10 days post-implantation of the electrodes. Subjects are provided with free access to food and water during testing.

Subjects are generally tested during daylight hours in a testing chamber. The testing chamber can be insulated from the general laboratory environment, e.g. it can be housed in a sound-attenuating chamber, to attenuate external stimuli. Animals are preferably first habituated to the testing chamber prior to experimentation, by transferring the animals to the testing chamber for a period of at least 30 minutes for at least 3 days. Baseline measurements (e.g. electrical potential recordings) are established, and a compound is administered to the subject. Measurements of one or more components of the electromagnetic response may be taken prior to, during, and after administering the stimulus.

The monitored electrical potentials can be amplified and recorded digitally, using standard EEG recording hardware. The recorded electrical potentials can be processed, filtered, and analyzed digitally, using custom made software. The evoked-response potentials described herein are constructed from peristimulus time histograms. In one embodiment of the present invention, stimulation intensity that provides a distinct, though not large, ERP (filtered at approximately 0.5-150 Hz) is first confirmed from a number of stimulations, e.g. more than 50 stimulations provided at greater than or equal to 0.1 Hz. Stimulus current (e.g., 0.01-10.0 mA) is then adjusted to produce ERPs that are at least detectable from background electrical activity. For purposes of the present invention, "background electrical activity" refers to baseline electrical (ERP) activity, which is recorded in the absence of electrical stimulation and the absence of candidate chemical compound.

In one example of the present invention, following the calibration of subiculum/CA1 stimulation intensity, ERPs are then collected from one, two, or more time blocks that include a period of electrical stimulation followed by a period of no stimulation. In one example, the time blocks are 15-minute blocks comprised of 10-minutes of hippocampal stimulation (0.2 Hz=150 stimulations) followed by 5-minutes of no stimulation. The electrical stimulation may be performed, using standard laboratory protocols, e.g., with a current of between about 0.01 mA and about 10.0 mA, a duration of between about 0.01 ms (milliseconds) and about 10.0 ms, and a frequency of between about 0.1 Hz and about 10 Hz.

In one preferred example, following baseline recordings, vehicle (e.g. saline) or a putative cognition modulating compound (i.e. cognition enhancing compound such as MPH or other candidate drug) are administered. ERPs are recorded in 15-min blocks described above for the next 60-90-minutes. Graphs of ERPs are produced. Plots of ERPs can then be compared with baseline recordings (see, e.g., FIG. 1). This experimental run may be repeated for multiple compound doses or repeated measurements. As well, measurements can be taken at different times after administration of the compound to the subject.

The example shown in FIG. 1 illustrates the effects of saline (control compound) or the cognition-enhancing compound, Methylphenidate (MPH), on the evoked response potential (ERP) recorded within the prefrontal cortex of *Rat-*

*tus norvegicus* Sprague-Dawley. Each of the three plots illustrates the effect of an intraperotoneal (i.p.) injection of saline (0.9% w/v, top) an i.p. injection of a cognition-enhancing dose of MPH (0.5 mg/kg, Middle), and an i.p. injection of a cognition-impairing dose of MPH (2.0 mg/kg, Bottom). For each plot the average effect of these compounds over 0-30 min (black diamond) and 60-90 min (open box) following injection is illustrated. The numerical values in each plot represent the difference in absolute value of the mean ERP between pre- and post-compound administration. A clearly visible and distinct change from baseline is observed only during 0-30 post-MPH period when this compound exerts a cognition-enhancing effect. The x-axis shows time bins in ms following the onset of afferent stimulation; the y-axis shows the difference in absolute value of the mean ERP between pre- and post-compound administration for each time bin.

Variations of the ERP stimulus parameters can be used in the practice of the present invention. For example, it is possible to vary the duration of the stimulation trains (i.e. shorter or longer stimulation trains), the duration of the stimulation periods and the no-stimulation periods (i.e. shorter or longer stimulation trains with longer or shorter no-stimulation periods), the intensity of the stimulation, the number of the applied stimuli, the frequency of the applied stimuli, etc. If desired, similar experimental runs may be repeated for multiple compound doses or to obtain repeated measurements.

In one example, changes in ERPs can be calculated from trial-bin counts used to generate peristimulus time histograms (PSTHs). In one example, data are collected from non-sleep EEG states only, as determined from field potential recordings, or in combination with video or other activity measurements. In one example, each PSTH is generated from randomly selected stimulus presentations. Data can be expressed as a percentage of baseline ERP activity (pre-vehicle or pre-administration of chemical compound) and percentage change from control (e.g. saline), which permits comparisons between subjects with different magnitudes of ERPs and/or different shapes of ERPs.

Appropriate statistical comparisons, including but not limited to mixed two-way ANOVA with both repeated (time)- and between (treatments)-measures, can be used to determine statistical significance of candidate compound-induced changes in PFC. Analysis of the ERPs as a function of dose and time and post-hoc comparisons can be performed (i.e. Fisher LSD test). A "statistically significant difference" means there is statistical evidence that there is a difference; it does not mean the difference is necessarily large, important or significant in the usual sense of the word.

FIG. 3 is a schematic of one preferred embodiment of the present invention. Illustrated is an example embodiment that can be used to record evoked electrical responses from the prefrontal cortex elicited by ventral subiculum (a region of the hippocampus formation) stimulation. The embodiment in FIG. 3 shows a host computer with recording and stimulus generating software 302. The host computer may be connected to a programmable stimulator 312 and to an amplifier 304. The electrical signal from electrodes and synchronization pulses from stimulator 312 may be saved to storage media 304. Preferably, a separate data storage device 306 is provided. In preferred embodiments, prefrontal cortex recordings are taken on the ipsi- and/or contra-lateral side of the stimulator 308. The stimulating electrode is preferably placed within the ventral subiculum 310.

Figure 4:
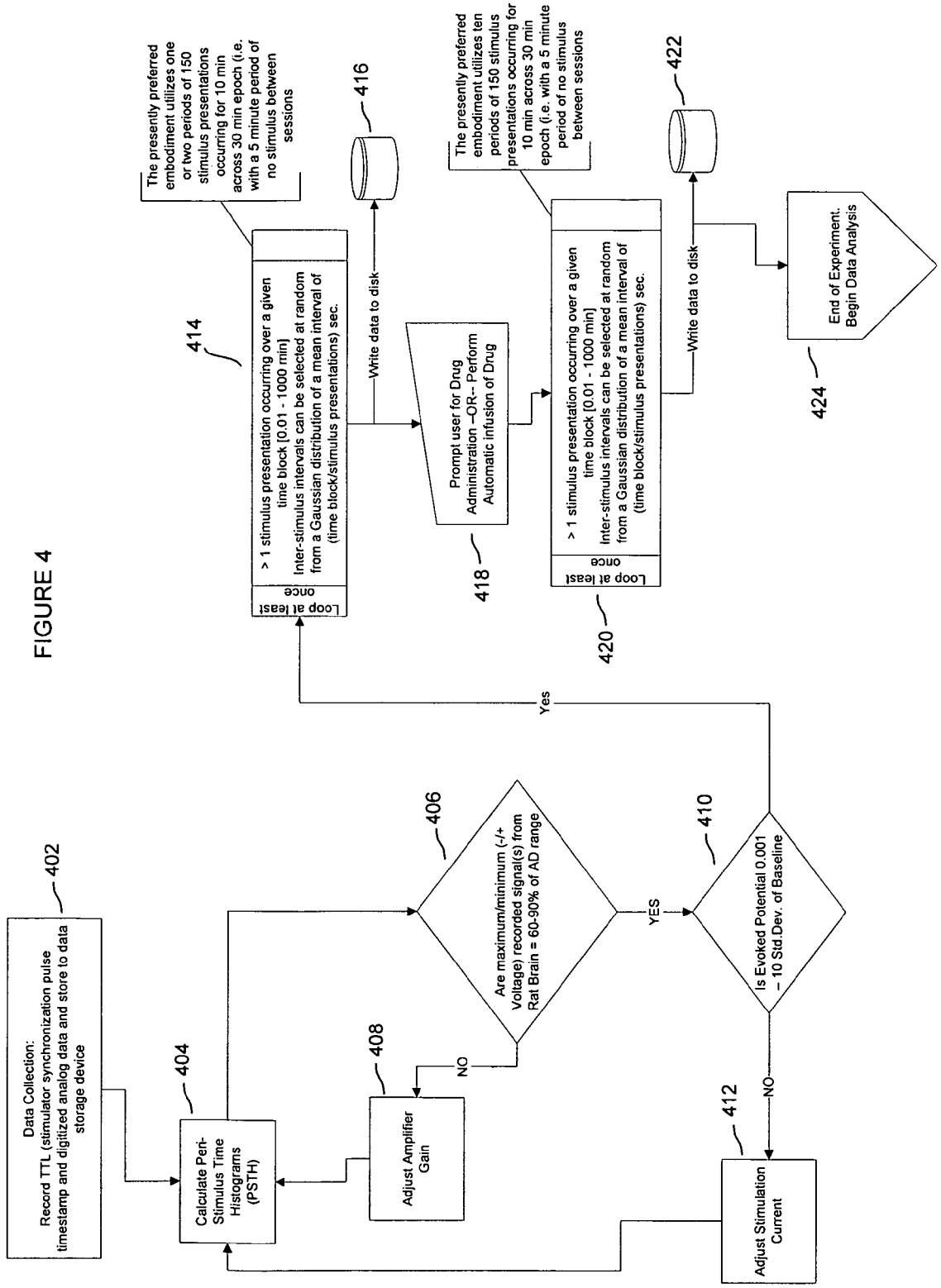
FIG. 4 is a block flow diagram of one embodiment of the data collection and control module software used for practicing the methods of the present invention.
Figure 5:
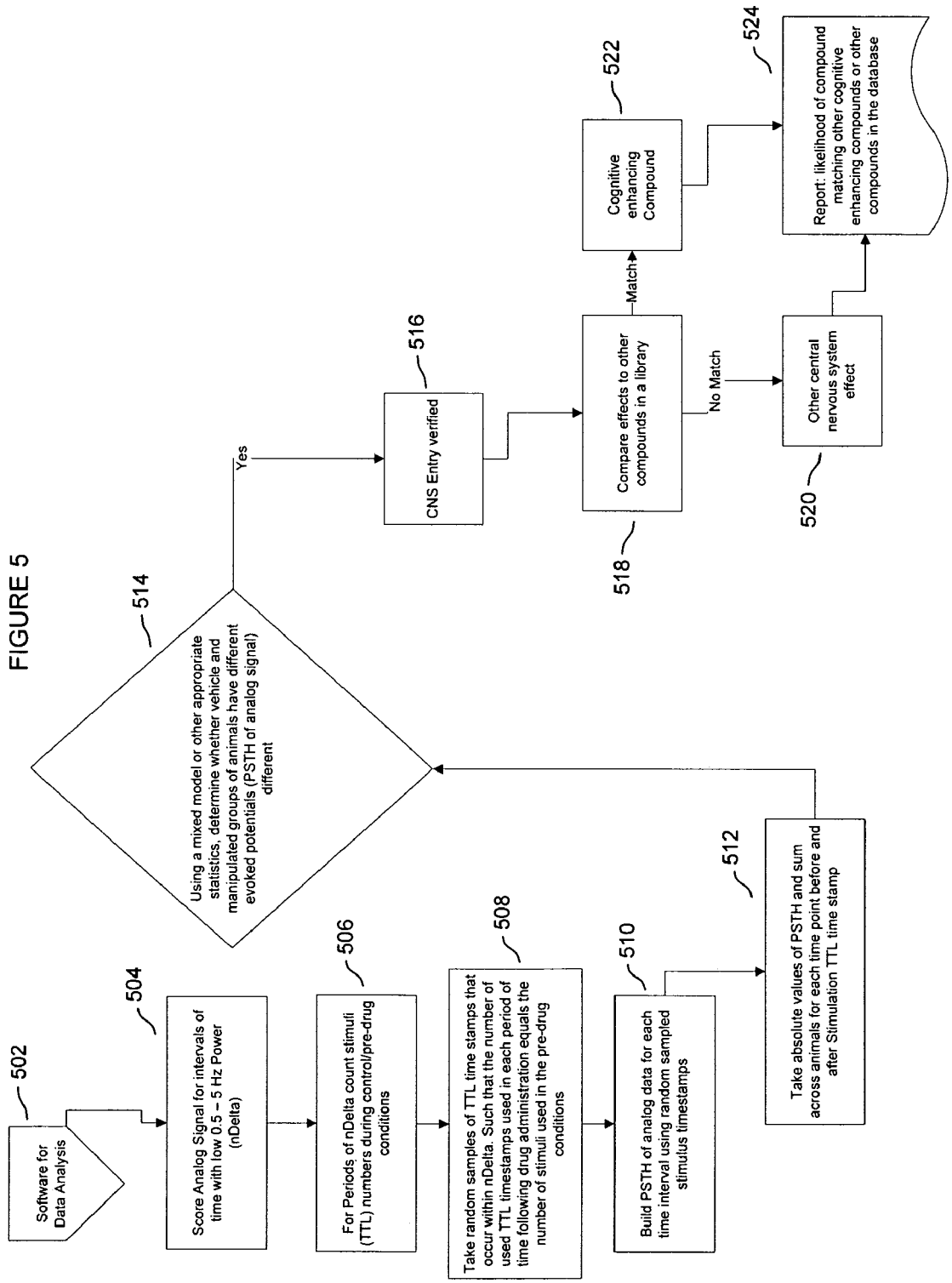
FIG. 5 is a block flow diagram of another embodiment of the data analysis software used for practicing the methods of the present invention.

FIGS. 4 and 5 are block flow diagrams of exemplary embodiments of the data collection and analysis software used for practicing the methods of the present invention.

FIG. 4 is a schematic of one preferred embodiment of the workflow used to collect data in the present invention. Illustrated in FIG. 4 is an example embodiment that can be used to record evoked electrical responses from the prefrontal cortex (PFC) elicited by ventral subiculum (a region of the hippocampus formation) stimulation prior to and following administration of a compound (drug). In the embodiment shown in FIG. 4, from the collected data 402, peristimulus time histograms are calculated 404. If the maximum/minimum voltage values for the recorded signals from the brain are not within 60-90% of the AD range, then the amplifier gain is adjusted 408. If the maximum/minimum voltage values for the recorded signals from the brain are within 60-90% of the AD range, then a determination is made whether the evoked potential is within 0.001-10 standard deviations of the baseline 410. If it is not, then the stimulation current is adjusted 412. If it is, then more than one stimulus is presented over a given time block 414. The data is preferably written to disc 416. The user is preferably prompted for drug administration or automatic infusion of drug is performed 418. Then, more than one stimulus is presented over a given time block 420. The data is preferably written to disc 422. The experiment ends and the data is then analyzed 424.

FIG. 5 is a schematic of one preferred embodiment of the workflow used to analyze data in the present invention. Illustrated is an example embodiment that can be used to analyze evoked electrical responses from the prefrontal cortex (PFC) elicited by ventral subiculum (a region of the hippocampus formation) stimulation prior to and following administration of a compound (drug). This schematic additionally illustrates an example embodiment that can be used to determine the degree to which a compound (drug) is active within the brain (CNS Entry) and/or matches known or to be determined effects on PFC cellular activity.

In the embodiment shown in FIG. 5, software for data analysis 502 is preferably used to score analog signals for intervals of time with low 0.5-5 Hz power 504. The stimuli numbers are counted for the same time intervals during control, i.e. pre-administration of drug conditions 506. Random samples of time stamps are taken, such that the number of time stamps used in each period of time following drug administration equals the number of stimuli used in the pre-drug conditions 508. A graphical representation, such as a peristimulus time histogram of analog data for each time interval using random sampled stimulus time stamps, may then be built 510. The absolute values of the peristimulus time histogram and the sum across animals for each time point before and after stimulation time stamps is then taken 512. A mixed model or other appropriate statistics is used, to determine whether vehicle and manipulated groups of animals have different evoked potentials 514. If they have, then the central nervous system is verified 516. The effects may then be compared to other compounds, preferably from a library 518. If there is a match, then it is determined that the compound is deemed a cognitive enhancing compound is 522. If there is no match, then it is determined that there is some other central nervous system effect 520. A report is preferably generated on the likelihood of the compound matching other cognitive enhancing compounds or other compounds in the database 524.

Uniqueness of ERP recordings. The methods of the present invention are preferably practiced using field potentials measurements (i.e., ERPs). Even though it may be possible to use single-unit (i.e., single neuron) recordings, such recordings do not necessarily predict what will be measured in ERP measurements under similar experimental conditions. Evidence suggests that the observations of electrical activity of an individual neuron in the frontal cortex of the rat have little predictive value toward that observed in an evoked-response potential (e.g., Klausberger et al., 2003, *Nature* 421: 844-848). Within the subject's frontal cortex there exist many different populations of cell types and activity patterns of these neurons. For example, there exist excitatory and inhibitory neurons, both demonstrating a variety of morphologies that confer unique spontaneous discharge patterns and responses to incoming stimuli. These neurons exhibit responses to incoming stimuli with short and/or long latency excitatory discharge, a reduction in spontaneous discharge, and even an initial evoked-excitatory response, followed by an inhibition in discharge rates. Thus, sampling any neuron from this myriad of neurons with numerous possible discharge patterns does not necessarily correlate well with field potentials that comprise the basis for an ERP.

The field potential that is used to generate the ERP is a continuous function. One would find a very poor correlation between the discharge of a single neuron and a given field potential signature or vice versa. In other words, the stochastic nature of the neuron and the electrical discharge of a neuron correlate poorly with specific components of the field potential. ERPs are much easier to record and thus they offer a much better screen of cognition-modifying compounds. In addition, observations of electrical activity of an individual neuron in the frontal cortex of the rat have little predictive value toward that observed in an evoked-response potential, because neuronal discharge is a combination of stochastic and deterministic processes leading to a point process in time. Thus, a reasonable practitioner of the art would not suggest that recordings of individual neurons would work as equally well as a determinant or predictor of cognitive enhancing compounds.

To aid understanding of the present invention, Table 1 provides a glossary of abbreviations and technical terms used herein.

TABLE 1

Abbreviations

| Abbreviation | Means |
| --- | --- |
| ADHD | Attention Deficit/Hyperactivity Disorder |
| ANOVA | Analysis of variance |
| CNS | Central nervous system |
| ECoG | Electrocorticogram |
| EEG | Electroencephalogram |
| ERP | Evoked-response potential |
| GABA | Gamma-aminobutyric acid |
| MPH | Methylphenidate |
| PFC | Prefrontal cortex |
| PSTH | Peristimulus time histogram |

It is to be understood that this invention is not limited to the particular methodology, protocols, subjects, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention.

EXAMPLES

Animals and Surgery

Male Sprague-Dawley rats (250-350 g) were surgically implanted with 1-4 EEG recording electrodes into the pre-limbic region of the PFC (coordinates: A +3.0±1.0 mm; L 0.8±0.3 mm; V −3.0) and a stimulation electrode into the subiculum/CA1 region of the hippocampus (coordinates: A −6.7; L 5.5; V −6.5). EEG signals were referenced to a ground electrode. Electrodes were held in place with acrylic cement and the animals were allowed to recover for 5-10 days prior to the measurements. Animals were provided with free access to food and water during testing.

Recording Sessions

Animals were tested during daylight hours in a Plexiglas testing chamber (32×32×40 cm) housed in a sound-attenuating chamber. Animals were first habituated to the testing chamber prior to experimentation. Field potentials/EEG signals were amplified and recorded digitally.

ERPs were constructed from peristimulus time histograms. Stimulation intensity that provides a distinct, though not large, ERP (filtered approx. 0.5-150 Hz) was first confirmed from greater than or equal to 50 stimulations that were provided at greater than or equal to 0.1 Hz. Stimulus current (0.1-3.0 mA) from a constant current source was adjusted to produce ERPs that were at least detectable from background electrical activity. Following this calibration of subiculum/CA1 stimulation intensity, ERPs were then collected from one or two 15-minute blocks comprised of a 10-min of hippocampal stimulation period (0.2 Hz=150 stimulations) followed by 5-minutes of no stimulation. Following baseline recordings, vehicle or a putative cognitive enhancing compound (i.e., psychostimulant such as MPH or other drugs) were administered. ERPs were recorded in 15-min blocks described above for the next 60-90-minutes.

Changes in ERPs were calculated from trial-bin counts used to generate peristimulus time histograms (PSTHs). Data were collected from non-sleep EEG states only, as determined from field potential recordings or in combination with video or other activity measurements. Each PSTH was generated from randomly selected stimulus presentations. Data were expressed as a percentage of baseline ERP activity (pre-vehicle or pre-MPH) and percentage change from saline, which permits comparisons between subjects with different magnitude/shape ERPs.

Appropriate statistical comparisons, including mixed two-way ANOVA with both repeated (time)—and between (treatments)—measures, were used to determine statistical significance of candidate compound-induced changes in PFC. Analyses of ERPs as a function of dose and time and post-hoc comparisons were performed (i.e., Fisher LSD test).

The graphs in FIG. 1 show the effects of 0.5 mg/kg methylphenidate (MPH), a cognition-enhancing dose of this drug, and 2.0 mg/kg MPH, a dose that lacks cognition-enhancing effects, vs. saline (control injection) on the evoked-response potential recorded in the ipsilateral hemisphere of the prefrontal cortex following electrical stimulation of the ventral subiculum of the hippocampus in a rat. The subiculum is the most inferiorly located component of the hippocampal formation. The data in FIG. 1 are expressed as millivolt (mV) change from baseline values, which are pre-treatment recordings. Data are from 0-30-minutes and 60-90-minutes post-intraperitoneal injection. Note that the dose of 0.5 mg/kg MPH is clinically relevant, exerting cognition-enhancing effects in rats, whereas 2.0 mg/kg MPH exceeds clinical relevance, lacking cognition-enhancing actions. In the 30-60 minute period following drug treatment, a number of components of the ERP were different from that observed during pre-treatment recordings (baseline). Similar effects of MPH were observed (i.e., similar ERP recordings were obtained) within the ipsilateral and contralateral hemispheres of the PFC, relative to the hippocampal stimulation electrode.

These analyses indicate that cognition-enhancing doses of MPH alter the magnitude of specific components of the ERP that are not observed with higher doses that do not improve PFC-dependent cognition. The selective facilitation of PFC neuronal responsiveness apparent at the level of an ERP creates the potential to readily identify compounds that can be used as cognitive modulators, thus offering a low-tech screen for cognition-modulating actions of compounds that would be appropriate for drug discovery programs. This offers the possibility of relatively high-throughput screening of compounds, comparable to other in vivo assays currently used in drug discovery programs in the majority of pharmaceutical companies. This discovery also provides a potential tool for the development of new drugs for the treatment of ADHD and other disorders or conditions associated with impairment in PFC-dependent cognition. Both compounds that might enhance PFC-dependent cognition and compounds that might impair PFC-dependent cognition can be identified using the methods of the present invention.

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters, obvious to those skilled in the art of electrophysiology, neurophysiology, and cognitive psychology, are within the scope of this invention. All publications, patents, and patent applications cited herein are incorporated by reference in their entirety for all purposes.

What is claimed is:

1. A method of testing a subject to predict an effect of an administered compound on the subject's prefrontal cortex-dependent cognition, which comprises:
    administering a compound;
        subsequently administering a stimulus that evokes an electromagnetic response in the subject's prefrontal cortex;
        sensing at least one component of the electromagnetic response in the subject's prefrontal cortex independent from electromagnetic responses in other areas of the brain in response to the administered stimulus both in the presence and in the absence of the compound;
        comparing the at least one component of the electromagnetic response from the prefrontal cortex evoked by the stimulus in the absence of the administered compound with the at least one component of the electromagnetic response from the prefrontal cortex evoked by the stimulus in the presence of the administered compound; and
    determining the effect of the administered compound based on the comparison.

2. The method of claim 1 wherein determining the effect of the administered compound comprises correlating the at least one component of the electromagnetic response evoked by the stimulus with the effect of the administered compound on the subject's prefrontal cortex-dependent cognition.

3. The method of claim 1 wherein the at least one component of the electromagnetic response is an electrical component.

4. The method of claim 1 wherein the stimulus is selected from the group consisting of electrical, magnetic, photic, auditory, or mechanical stimulation of the subject's nervous system.

5. The method of claim 1 wherein the sensing of the at least one component of the electromagnetic response comprises measuring field potentials of the prefrontal cortex.

6. The method of claim 1 wherein the sensing of the at least one component of the electromagnetic response comprises electroencephalography or magnetoencephalography.

7. The method of claim 1 wherein the administering the stimulus comprises an electrical stimulation of the subject's hippocampus.

8. The method of claim 1 wherein the administering of the stimulus comprises an electrical stimulation with a current of between about 0.01 mA and about 10.0 mA, a duration of between about 0.01 ms and about 10.0 ms, and a frequency of between about 0.1 Hz and about 10 Hz.

9. The method of claim 1 wherein the administered compound enhances the prefrontal cortex-dependent cognition.

10. The method of claim 1 wherein the administered compound impairs the prefrontal cortex-dependent cognition.

11. The method of claim 1 wherein sensing the at least one component of the electromagnetic response in the subject's prefrontal cortex in response to the administered stimulus in the absence of the compound comprises:
    administering the stimulus; and
    sensing the at least one component of the electromagnetic response, the sensing being performed prior to administering the compound.

12. The method of claim 1 wherein administering the stimulus is performed during sensing the at least one component of the electromagnetic response in order to obtain the at least one component of the electromagnetic response prior to, during, and after administering the stimulus.

13. A method of testing a subject to predict an effect of an administered compound on the subject's prefrontal cortex-dependent cognition, which comprises:
    administering a compound;
        subsequently administering a stimulus that evokes an electromagnetic response in the subject's prefrontal cortex;
        sensing at least one component of the electromagnetic response in the subject's prefrontal cortex independent from electromagnetic responses in other areas of the brain in response to the administered stimulus both in the presence and in the absence of the compound;
        comparing the at least one component of the electromagnetic response from the prefrontal cortex evoked by the stimulus in the presence of the administered compound to at least one component of the electromagnetic response from the prefrontal cortex evoked by the stimulus when a known cognition modulator is administered to the subject; and
    predicting the effect of the administered compound on the subject's prefrontal cortex-dependent cognition based on the comparison.

14. The method of claim 13 wherein the known cognition modulator is methylphenidate.

15. The method of claim 13 wherein the stimulus is selected from the group consisting of electrical, magnetic, photic, auditory, or mechanical stimulation of the subject's nervous system.

16. The method of claim 13 wherein the sensing of the at least one component of the electromagnetic response comprises measuring field potentials of the prefrontal cortex.

17. The method of claim 13 wherein the sensing of the at least one component of the electromagnetic response comprises electroencephalography or magnetoencephalography.

18. The method of claim 13 wherein the administering the stimulus comprises an electrical stimulation of the subject's hippocampus.

19. The method of claim 13 wherein the administering the stimulus comprises an electrical stimulation with a current of between about 0.01 mA and about 10.0 mA, a duration of between about 0.01 ms and about 10.0 ms, and a frequency of between about 0.1 Hz and about 10 Hz.

* * * * *